United States Patent [19]

Grady et al.

[11] Patent Number: 4,649,560
[45] Date of Patent: * Mar. 10, 1987

[54] DIGITAL X-RAY STAND

[75] Inventors: John K. Grady, c/o XRE Corporation, 300 Foster St., Littleton, Mass. 01460; Paul G. Rice, Lincoln; Kip P. Van Steenburg, Wayland, both of Mass.

[73] Assignee: John K. Grady, Littleton, Mass.

[*] Notice: The portion of the term of this patent subsequent to Sep. 10, 2002 has been disclaimed.

[21] Appl. No.: 575,204

[22] Filed: Jan. 30, 1984

[51] Int. Cl.$^4$ ............................................. H05G 1/02
[52] U.S. Cl. ..................................... 378/196; 378/197
[58] Field of Search .............. 378/20, 17, 15, 195-198

[56] References Cited

U.S. PATENT DOCUMENTS

| 1,573,571 | 2/1926 | Pohl | 378/196 |
|---|---|---|---|
| 2,818,510 | 12/1957 | Verse | 378/189 |
| 3,281,598 | 10/1966 | Hollstein | 378/196 |
| 3,670,163 | 6/1972 | Lajus | 378/196 |
| 4,315,146 | 2/1982 | Rudin | 378/146 |
| 4,426,725 | 1/1984 | Grady | 378/197 |
| 4,534,051 | 8/1985 | Grady et al. | 378/99 |
| 4,541,108 | 9/1985 | Grady et al. | 378/196 |

Primary Examiner—Janice A. Howell
Attorney, Agent, or Firm—James H. Grover

[57] ABSTRACT

An X-ray tube and receptor are held on opposite ends of a two-limbed carriage mounted on a sliding arm. The arm is carried on a rotating support, the arm extending parallel to the rotational axis of the support. The two-limbed carriage pivots on the arm about a second axis perpendicular to the rotational axis and to a radiation axis extending between the X-ray tube and receptor.

17 Claims, 2 Drawing Figures

DIGITAL X-RAY STAND

BACKGROUND OF THE INVENTION

Stands for rotatively and reciprocally supporting X-ray tubes and X-ray receptors on opposite sides of a patient or other radiographic subject are exemplified in the prior art by United States patents to Verse, U.S. Pat. No. 2,818,510; to Hollstein, U.S. Pat. No. 3,281,598; to John K. Grady, U.S. Pat. No. 3,892,967 and by the copending application Ser. No. 376,109 of John K. Grady, now U.S. Pat. No. 4,426,725. These X-ray stands are useful for some types of radiographic examinations, but there is a need for an X-ray stand allowing better unilateral access to the patient, and it is one obJect of the present invention to provide such a stand.

A further object is to provide a stand which also controls positioning of the subject with reference to the stand.

SUMMARY OF THE INVENTION

According to the invention radiological apparatus for examination of a subject comprises a base; a support mounted on the base for rotation about a first axis; and an arm on the support extending parallel to the first rotation axis; a two-limbed carriage on the support with limbs extending to positions on opposite sides of the first rotation axis, the limbs holding radiation source means and radiation receptor means respectively on a radiation axis; and bearing means mounting the carriage on the arm for rotation about a second axis intersecting the first rotation axis, whereby rotation of the support and arm about the first axis and the two-limbed carriage about the second axis allow radiation of a subject from substantially throughout spherical loci around the subject while maintaining the angular relation of the radiation means to the rotational axis.

DRAWINGS

DESCRIPTION

Figure 1:
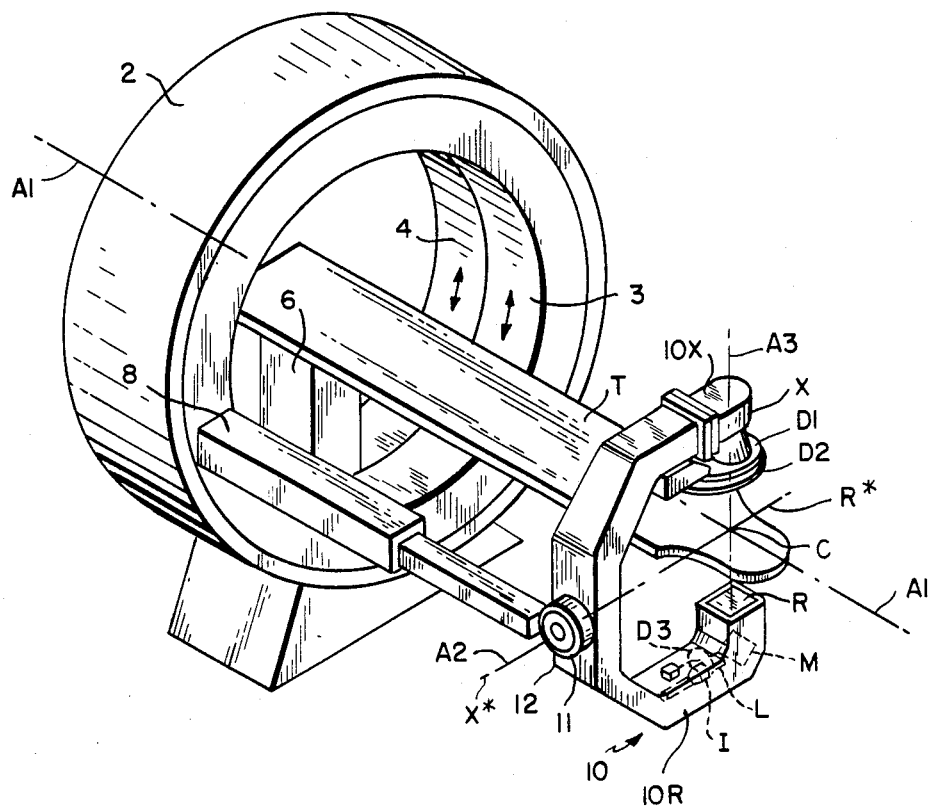
FIG. 1 is an isometric view of an X-ray stand according to the invention.
Figure 2:
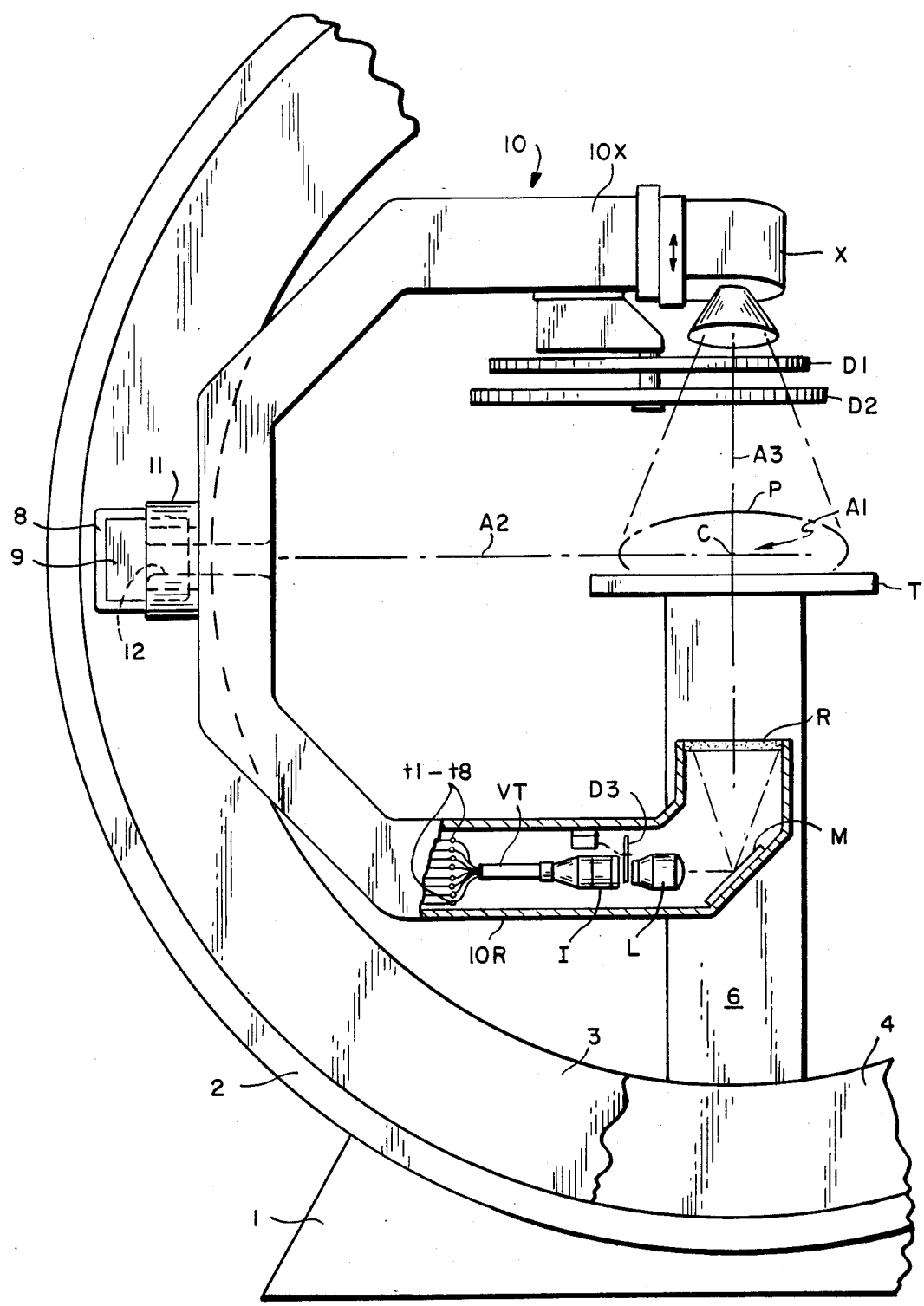
FIG. 2 is an end elevation of the stand partly broken away.

The X-ray stand shown in FIGS. 1 and 2 comprises a base 1 on which is fixed an outer ring 2. A front ring 3 and a rear ring 4 rotate within the outer ring 2 about an axis A1 by manual or motor drive. Extending radially inwardly from the rear ring 4 is a pedestal 6 bearing a table T for a patient or other subject at a position P above the table. The table extends and is longitudinally adjustable parallel to the rotation axis A1. Fixed to and extending at a right angle from the outer ring 2, parallel to the rotation axis A1, in a rectangular sleeve 8 in which an arm 9 slides preferably by motor drive. The outer end of the arm is connected to a two-limbed carriage 10 of C-shape or U-shape, by a rotary bearing 11 which has an aperture 12 on its axis A2 for a purpose to be described.

The two-limbed carriage 10 carries an X-ray tube X at one end and an X-ray receptor R at its opposite end, the tube and receptor being aligned on a radiation axis A3 intersecting the rotation axes A1 and A2 at an isocenter C somewhat above the table T and within the patient position P.

On the X-ray tube limb 10X of the carriage 10 are two rotating, X-ray opaque disks D1 and D2 with apertures transmitting a moving fan-shaped beam of X-rays, described in U.S. Pat. No. 4,315,146 and U.S. Pat. No. 4,534,051 of John K. Grady and Richard E. Rice, which has the advantage of reducing X-ray exposure of the patient. The X-ray receptor R beyond the patient on the opposite receptor arm 10R of the carriage 10 preferably comprises a scintillation screen R converting received X-rays into a secondary light image. The light image is reflected by a mirror M to a lens L. The lens L focusses the light on the input face of an image intensifier I coupled to a video tube generating digital video signals corresponding to the secondary image at its output terminals t1 to tn for connection to data processing equipment and video displays, for example. Between the lens L and image intensifier I is a third rotating light masking disk D3 with an aperture synchronized with those of the X-ray opaque disks D1 and D2.

The radiation set of X-ray tube and receptor can be angulated around the isocenter C on spherical loci by rotation of the front ring 3 about the ring rotation axis A1, and about the two-limbed carriage axis A2. The carriage can be reciprocated parallel to the ring rotation axis A1 without altering the angulation.

The present structure affords rotation of the radiation source means X and receptor R about both the first axis A1 and second axis A2 for radiation of a subject from substantially throughout spherical loci around the subject position at the isocenter C.

The aperture 12 along the carriage axis A2 is of a size to allow radiation therethrough between a second set of an X-ray tube X* and receptor R* at location shown in FIG. 1 on the axis A2.

It should be understood that the present disclosure is for the purpose of illustration only and that this invention includes all modifications and equivalents which fall within the scope of the appended claims. The arrangement of X-ray receptor R, mirror M, lens L and image intensifier are disclaimed.

We claim:

1. Radiological apparatus for examination of a patient comprising:
   a base;
   a first support mounted on the base for rotation about a first axis;
   a table having a patient foot end and a patient head end along the first axis, the table being cantilever supported at one end and unsupported at the other end;
   an arm attached to the support at one end only extendable along one side only of the table substantially the length of the table parallel to the first rotation axis from the supported end of the table to the unsupported end and leaving the other side of the table unobstructed;
   a two-limbed carriage on the arm with limbs extending to positions on opposite sides of the first rotation axis, the limbs holding radiation source means and radiation receptor means respectively on a radiation axis; and
   bearing means mounting the carriage on the arm for rotation about a second axis intersecting the first rotation axis, such that rotation of the support and arm about the first axis and the two-limbed carriage about the second axis allow radiation of a subject from substantially throughout spherical loci around the patient while maintaining the angular relation of the radiation means to the rotational axis without obstruction of access to the patient by the rotating support.

2. Apparatus according to claim 1 wherein the support is rotatable through at least 180 degrees for reversal of the radiation means.

3. Apparatus according to claim 1 wherein the radiation means are held on a radiation axis intersecting the rotation axis.

4. Apparatus according to claim 3 wherein the carriage is pivoted on the arm for adjustment of the angle of intersection of the rotation and radiation axes.

5. Apparatus according to claim 1 wherein the support is a ring rotatable through 360 degrees on the base.

6. Apparatus according to claim 1 including a second arcuate support on the base rotating on the same axis as the first said support and mounting a radiation transparent table for a subject under radiological examination.

7. Apparatus according to claim 1 including a second, arcuate support mounted on the base and a subject table mounted on the second support.

8. Apparatus according to claim 7 wherein the second, arcuate support is rotatable on the same axis as the first support.

9. Apparatus according to claim 1 wherein the carriage is rotatably mounted on the arm to turn on an axis normal to the arm.

10. Apparatus according to claim 9 wherein the carriage is mounted on the arm by a bearing having an aperture therethrough concentric with the axis of rotation of the bearing and carriage and the receptor has a radiation responsive area, the aperture being of size to transmit X-radiation therethrough over the area of the receptor.

11. Apparatus according to claim 1 including means slidingly attaching the arm to the support for reciprocation parallel to the first rotation axis toward the unsupported table end.

12. Apparatus according to claim 2 including means slidingly attaching the arm to the support for reciprocation parallel to the first rotation axis.

13. Apparatus according to claim 12 wherein the support is rotatable through at least 180 degrees for reversal of the radiation means.

14. Apparatus according to claim 12 wherein the radiation means are held on a radiation axis intersecting the rotation axis.

15. Apparatus according to claim 12 wherein the first support is a ring rotatable through 360 degrees on the base.

16. Apparatus according to claim 12 including a second arcuate support on the base rotating on the same axis as the first said support and mounting a radiation transparent table for a subject under radiological examination.

17. Apparatus according to claim 12 including a second arcuate support on the base and a subject table on the second support.

* * * * *